United States Patent [19]

Shetty

[11] 4,100,170

[45] Jul. 11, 1978

[54] ANORECTIC ADAMANTANE DERIVATIVES AND METHOD OF USING THE SAME

[75] Inventor: Bola Vithal Shetty, Rochester, N.Y.

[73] Assignee: Pennwalt Corporation, Philadelphia, Pa.

[21] Appl. No.: 171,736

[22] Filed: Aug. 13, 1971

Related U.S. Application Data

[62] Division of Ser. No. 691,182, Dec. 18, 1967, abandoned.

[51] Int. Cl.² .......................... A01N 9/20; A01N 9/24
[52] U.S. Cl. ..................................... 424/325; 424/330
[58] Field of Search .................. 424/330, 325; 260/563

[56] References Cited

U.S. PATENT DOCUMENTS

| | | | |
|---|---|---|---|
| 3,270,036 | 8/1966 | Bernstein et al. | 260/563 |
| 3,320,249 | 5/1967 | Bernstein | 260/563 |
| 3,489,802 | 1/1970 | Brake | 260/563 |
| 3,501,511 | 3/1970 | Narayanan | 260/563 |
| 3,929,888 | 12/1975 | Cashin et al. | 424/330 |
| 4,027,035 | 5/1977 | Cashin et al. | 424/330 |

OTHER PUBLICATIONS

Lunn et al., J. Chemical Soc. (1968) © pp. 1657–1660.

Primary Examiner—Albert T. Meyers
Assistant Examiner—D. W. Robinson
Attorney, Agent, or Firm—Edward A. Sager

[57] ABSTRACT

Adamantane derivatives such as β-(1-adamantyl)-α,α-dimethylethylamine hydrochloride, β-(1-adamantyl)-α-methylethylamine hydrochloride, d-β-(1-adamantyl)-α-methylethylamine hydrochloride, and 1-β-(1-adamantyl)-α-methylethylamine hydrochloride have anorectic activity.

The hydrazine derivatives of the above compounds are antihypertensive agents, and monoamine oxidase inhibitors.

5 Claims, No Drawings

ANORECTIC ADAMANTANE DERIVATIVES AND METHOD OF USING THE SAME

This application is a division of Ser. No. 691,182, filed Dec. 18, 1967 now abandoned.

The invention relates to adamantane derivatives, medicinal anorexigenic preparations containing the same, and the utilization of such preparations for curbing the appetite in animals.

Various compounds are known which are capable of curbing the appetite to cause weight losses, but these compounds have various disadvantages. Amphetamine, which is believed to have the highest anorexic activity, has disadvantages for certain people, particularly those where stimulation is undesirable.

An object of this invention is to provide an appetite suppressant preparation and method which curbs appetite in an animal without giving as great a stimulatory effect in equal dosage as amphetamine.

The appetite curbing compositions of the invention are comprised of a compound of the formula:

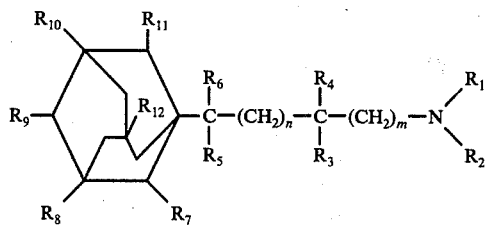

$R_1$ = H, lower alkyl, aralkyl, aralkyl substituted with $NH_2$, OH, $OCH_3$, halogen, alkyl, $NO_2$; phenoxyalkyl or phenoxyalkyl substituted with $NH_2$, OH, $OCH_3$, halogen, alkyl, or $NO_2$; acyl such as formyl or acetyl.

$R_2$ = H, lower alkyl, COO-lower alkyl, aralkyl, aralkyl substituted with $NH_2$, OH, $OCH_3$, halogen, alkyl, $NO_2$; phenoxyalkyl or phenoxyalkyl substituted with $NH_2$, OH, $OCH_3$, halogen, alkyl, or $NO_2$; acyl such as formyl or acetyl.

$R_1$ and $R_2$ can be joined together to form, with the nitrogen, a heterocyclic ring

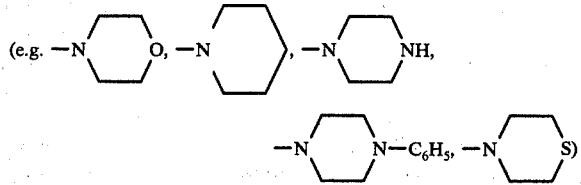

$R_3$ = H, lower alkyl, or alkynyl
$R_4$ = H, lower alkyl, or alkynyl
$R_5$ = H, OH, halogen, or lower alkyl
$R_6$ = H, OH, halogen, or lower alkyl
$R_5$ and $R_6$ together may represent a carbonyl oxygen
$R_7$ = H, lower alkyl, halogen, hydroxy, alkoxy, amino or substituted amino, trifluoromethyl, sulfamyl, nitro, phenyl
$R_8$, $R_9$, $R_{10}$, $R_{12}$ are any of $R_7$
$n$ = 0 to 4
$m$ = 0 to 4

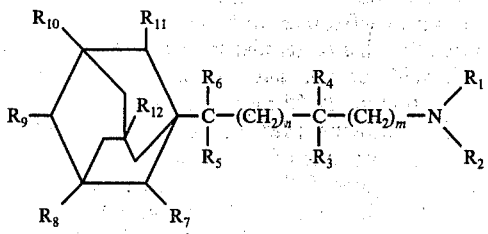

or their pharmaceutically acceptable acid addition salts, wherein:

$R_1$ = H, lower alkyl, aralkyl, aralkyl substituted with $NH_2$, OH, $OCH_3$, halogen, alkyl, $NO_2$; phenoxyalkyl or phenoxyalkyl substituted with $NH_2$, OH, $OCH_3$, halogen, alkyl, or $NO_2$; acyl such as formyl or acetyl.

$R_2$ = H, lower alkyl, COO-lower alkyl, aralkyl, aralkyl substituted with $NH_2$, OH, $OCH_3$, halogen, alkyl, $NO_2$; phenoxyalkyl or phenoxyalkyl substituted with $NH_2$, OH, $OCH_3$, halogen, alkyl, or $NO_2$; acyl such as formyl or acetyl.

$R_1$ and $R_2$ can be joined together to form, with the nitrogen, a heterocyclic ring

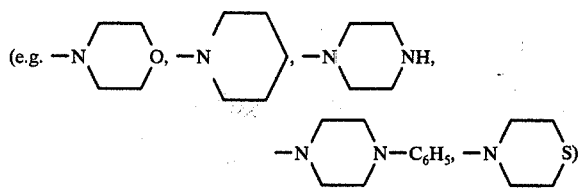

$R_3$ = H, lower alkyl, or alkynyl
$R_4$ = H, lower alkyl, or alkynyl
$R_5$ = H, OH, halogen, or lower alkyl
$R_6$ = H, OH, halogen, or lower alkyl
$R_5$ and $R_6$ together may represent a carbonyl oxygen
$R_7$ = H, lower alkyl, halogen, hydroxy, alkoxy, amino or substituted amino, trifluoromethyl, sulfamyl, nitro, phenyl
$R_8$, $R_9$, $R_{10}$, $R_{11}$, $R_{12}$ are any of $R_7$
$n$ = 0 to 4
$m$ = 0 to 4

The above compounds usually are mixed with a pharmaceutical carrier so that the composition for commercial use contains 0.5 to 20% of the compound.

The compositions are preferably adapted for peroral use for convenience, but may be used in other forms such as suppositories. The compositions are preferably in the form of tablets, capsules or suspensions for oral administration.

Examples of suitable inert pharmaceutical carriers are sugar syrups, potato starch, talcum, polyethylene glycols, and lactose.

Examples of suitable acids for forming the acid addition salts are hydrochloric acid, sulfuric acid, phosphoric acid, methane sulfonic acid, tartaric acid, citric acid, and the cation exchange resins such as the carboxylic acid, phosphonic acid, and sulfonic acid resins.

For sustained release, the acid addition salt (resinate) of the compound with a 3–10% cross-linked polystyrene sulfonic acid cation exchange resin gives good results. These resinates are easily made by simply contacting the base compound in aqueous suspension with the cation exchange resin.

The method of curbing the appetite comprises administering an effective amount of the compound of the above formula or its pharmaceutically acceptable non-toxic acid addition salt. The usual single dose is 10-50 mgm., preferably 25 mgm. of the said compounds.

The following examples are given to illustrate the active compounds of the invention. First the synthetic scheme is given, followed by the details of the preparation of each intermediate compound in the synthetic scheme through to the final active compound.

EXAMPLE 1

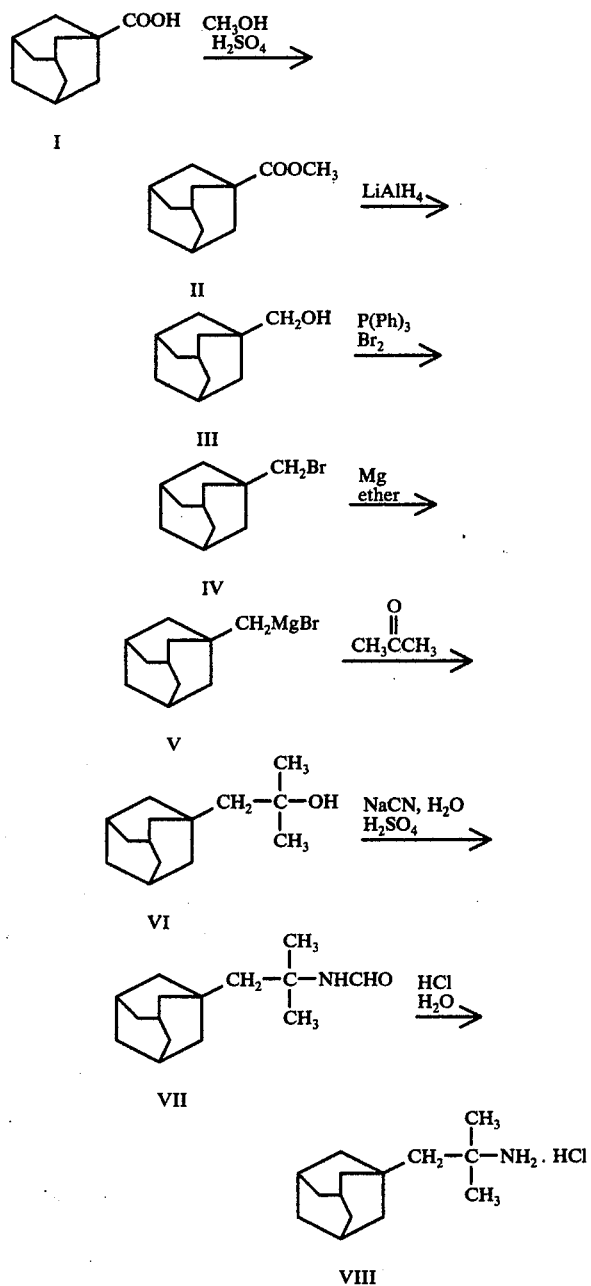

Preparation of Methyl-1-adamantanecarboxylate, II

A mixture of 1-adamantanecarboxylic acid (572 gm.), methanol (2.2 liters), and $H_2SO_4$ (90 ml.) was refluxed 5 hours and then cooled to room temperature overnight. The reaction mixture was poured into 28 liters of water and extracted with chloroform (2 × 150 ml. for each 3.5 liters of solution). The chloroform extracts were combined, washed with water, dried, and concentrated. The residual oil was distilled to give 476 gm. product (77.5% yield) $b_{17}$ approx. 143°.

Preparation of 1-Hydroxymethyladamantane, III

Methyl-1-adamantanecarboxylate (104 gm.) dissolved in 465 ml. anhydrous ether was added over a 2 hour period to 37.5 gm. lithium aluminum hydride in 753 ml. anhydrous ether. The mixture was stirred an additional 2 hours, cooled and water added gradually. The ether was separated. The water was extracted twice with ether and the combined ether layers dried and concentrated. The residual solid was dissolved in methanol and water was added to precipitate the product which was filtered and dried over $P_2O_5$ to give 80 gm., m.p. 113.5°-15.5°.

Preparation of 1-Bromomethyladamantane, IV

To 1-Hydroxymethyladamantane (366 gm.) and triphenylphosphine (598 gm.) in 1600 ml. dimethylformamide was added a solution of 366 gm. bromine in 800 ml. dimethylformamide over a 5 hour period. The mixture was left overnight at room temperature and then distilled (under aspirator) to remove solvent and product. The distillate was poured into 8 liters of water and filtered. The solid was dissolved in petroleum ether (30°-60°), washed with $K_2CO_3$ solution, then with water, dried, and concentrated to dryness. The residue recrystallized from 2.5 liters methanol gave 426.6 gm., m.p. 43°-4°. (1st crop plus additional crops obtained on concentration of the mother liquors.)

Preparation of Adamantane-1-tert-butanol, VI

Magnesium (80.2 gm.), 1290 ml. anhydrous ether, and a few grams of 1-bromo-methyladamantane were charged to a flask and heated to start the reaction. A solution of 186 gm. 1-bromomethyladamantane in 430 ml. anhydrous ether was added dropwise, with stirring and heating, over 2 hours and the mixture stirred another hour. The ether solution was decanted from unreacted magnesium, a solution of 44.8 gm. acetone in 320 ml. anhydrous ether was added dropwise over 2 hours, and stirring continued for another hour. The reaction mixture was cooled, a solution 44 gm. $NH_4Cl$ in 430 ml. water added dropwise, cooling to 15°, and the organic layer separated. The aqueous layer was extracted with ether, ether fractins combined, dried and concentrated to give a mixture of oil and solid. The oil was dissolved in methanol, filtered, left overnight at room temperature and refiltered and the solution concentrated. The methanol residue was distilled, and the distillate, $b_{0.025}$ 95°-110°, was dissolved in hot isopropanol (total volume about 250 ml.). Water was added to the hot solution until it became turbid. The solution was cooled and filtered and the filtrate diluted again to give a 2nd crop of solid. Combined 1st and 2nd crops totalled 90.5 gm. A second recrystallization gave 85 gm. of product (3 crops combined), m.p. 58°-8.5°.

|  | C | H | O |
|---|---|---|---|
| Calcd.: | 80.71 | 11.61 | 7.68 |
| Found: | 81.01 | 11.69 | 7.35 |

Preparation of N-formyl-β-(1-adamantyl)-α,α-dimethylethylamine, VII

Powdered sodium cyanide (19 gm.) was added, below 20°, to 42.5 ml. acetic acid, then a mixture of 42.5 ml. acetic acid and 45 ml. concentrated sulfuric acid was added dropwise. Cooling was stopped and adamantane-1-tert-butanol (70 gm.) was added in portions. The reaction mixture was heated ¾ hour at 85°–90°, stirred 2 hours at room temperature, cooled in an ice bath, and 550 ml. water added. The product was extracted with ether, the ether extract washed with dilute NaOH, then with water, dried and concentrated. The residue was dissolved in hexane (total volume 300 ml.) and the solution cooled to give a solid, m.p. 87°–8°. Concentration of the filtrate to 50 ml. gave a 2nd crop which was combined with the 1st crop to give 63 gm. of product.

|  | C | H | O | N |
|---|---|---|---|---|
| Calcd.: | 76.54 | 10.71 | 6.80 | 5.95 |
| Found: | 76.68 | 10.80 | 6.72 | 6.00 |

Preparation of β-(1-Adamantyl)-α,α-dimethylethylamine hydrochloride, VIII

N-Formyl-β-(1-adamantyl)-α,α-dimethylethylamine (63 gm.) was refluxed 4 hours with 905 ml. 2.7N HCl. The mixture was cooled and filtered to give the crude amine hydrochloride. The wet crude was stirred with 200 ml. CHCl$_3$, the CHCl$_3$ layer separated, dried, filtered, and hexane added to precipitate a solid which was filtered and dried. (The CHCl$_3$-hexane mother liquor was concentrated to give additional solid.) The precipitated solid was recrystallized from 100 ml. CHCl$_3$, dissolved in 700 ml. water, the solution washed with ether, made alkaline with dilute NaOH, extracted with CHCl$_3$, and the CHCl$_3$ washed, dried, and concentrated. The CHCl$_3$ residue was dissolved in 400 ml. ether and acidified with HCl gas. The solid was filtered and recyrstallized from 50 ml. CHCl$_3$ and dried under vacuum over P$_2$O$_5$ to give 9.8 gm. solid, m.p. 294°–5°.

|  | C | H | Cl | N |
|---|---|---|---|---|
| Calcd.: | 68.97 | 10.75 | 14.54 | 5.74 |
| Found: | 68.86 | 10.64 | 14.98 | 5.72 |
|  |  |  | 14.99 |  |
|  |  |  | 14.65 |  |
|  |  |  | 14.54 |  |

EXAMPLE 2

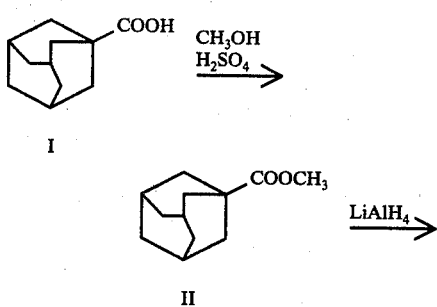

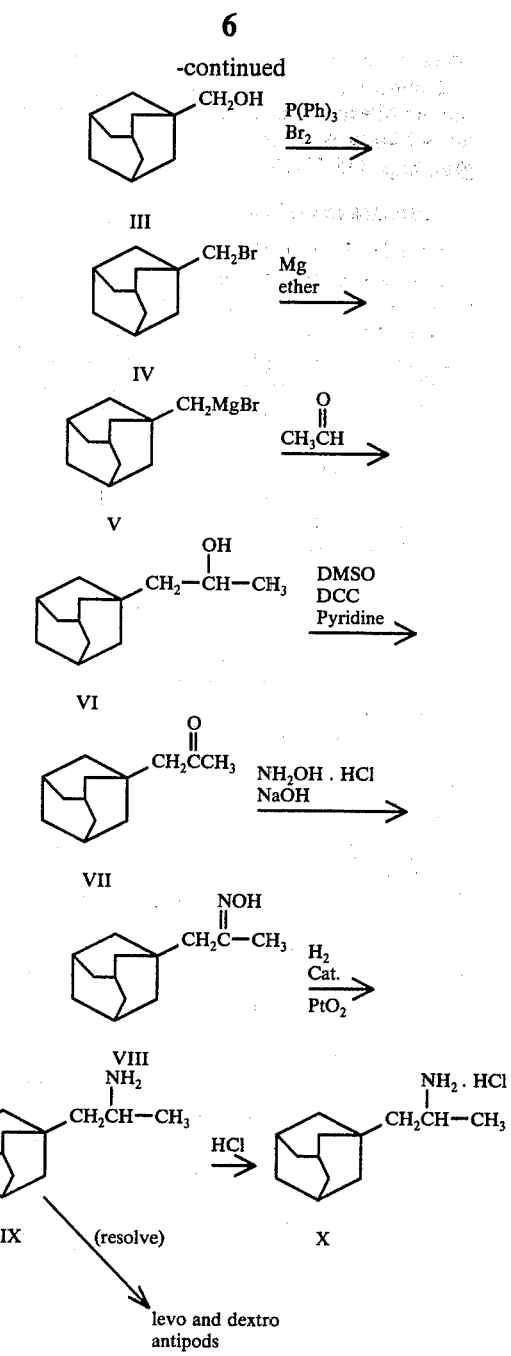

Preparation of Methyl-1-adamantanecarboxylate, II

A mixture of 1-adamantanecarboxylic acid (572 gm.), methanol (2.2 liters), and H$_2$SO$_4$ (90 ml.) was refluxed 5 hours and then cooled to room temperature overnight. The reaction mixture was poured into 28 liters of water and extracted with chloroform (2 × 150 ml.) for each 3.5 liters of solution). The chloroform extracts were combined, washed with water, dried, and concentrated. The residual oil was distilled to give 476 gm. product (77.5% yield) b$_{17}$ approx. 143°.

Preparation of 1-Hydroxymethyladamantane, III

Methyl-1-adamantanecarboxylate (104 gm.) dissolved in 465 ml. anhydrous ether was added over a 2 hour period to 37.5 gm. lithium aluminum hydride in 753 ml. anhydrous ether. The mixture was stirred an additional 2 hours, cooled and water added gradually. The ether was separated. The water was extracted twice with ether and the combined ether layers dried and concentrated. The residual solid was dissolved in methanol and water was added to precipitate the product which was filtered and dried over $P_2O_5$ to give 80 gm., m.p. 113.5°–15.5°.

Preparation of 1-Bromomethyladamantane, IV

To 1-Hydroxymethyladamantane (366 gm.) and triphenylphosphine (598 gm.) in 1600 ml. dimethylformamide was added a solution of 366 gm. bromine in 800 ml. dimethylformamide over a 5 hour period. The mixtue was left overnight at room temperature and then distilled (under aspirator) to remove solvent and product. The distillate was poured into 8 liters of water and filtered. The solid was dissolved in petroleum ether (30°–60°), washed with $K_2CO_3$ solution, then with water, dried, and concentrated to dryness. The residue recrystallized from 2.5 liters methanol gave 426.6 gm., m.p. 43°–4°. (1st crop plus additional crops obtained on concentration of the mother liquors.)

Preparation of Adamantane-1-isopropyl alcohol, VI

Magnesium (89.6 gm.), 75 ml. anhydrous ether and a few grams of 1-bromoethyladamantane were charged to a reaction flask and the mixture heated to start the reaction. Anhydrous ether (1440 ml.) was added, then a solution of 208 gm. 1-bromomethyladamantane in 480 ml. anhydrous ether was added over a 5 hour period. The ether solution was decanted from unreacted magnesium and a solution of 40.2 gm. acetaldehyde in 360 ml. anhydrous ether added dropwise over 2 hours. The mixture was cooled to 15° and a solution of 49.2 gm. $NH_4Cl$ in 480 ml. water added over ½ hour. The ether was separated, the aqueous layer extracted with ether and combined ether layers dried and concentrated. The ether residue was dissolved in methanol, filtered, left at room temperature overnight, refiltered and concentrated. The methanol residue was distilled to give a product $b_{0.1}$ 95°–120° which was recrystallized from 250 ml. hexane to give 61.6 gm. m.p. 56°–8°. Additional product was obtained by concentration of the mother liquor.

|        | C     | H     | O    |
|--------|-------|-------|------|
| Calcd.: | 80.35 | 11.41 | 8.23 |
| Found : | 80.50 | 11.43 | 8.30 |

Preparation of Adamantane-1-isopropyl ketone, VII

Adamantane-1-isopropyl alcohol (50 gm.), 20.6 ml. pyridine, 10.3 ml. trifluoroacetic acid, 387 ml. benzene, and 387 ml. dimethylsulfoxide were added to a reaction flask and 159 gm. dicyclohexylcarbodiimide was added over 5 minutes. The mixture was stirred overnight, a solution of 70 gm. oxalic acid in 650 ml. methanol added, and the reaction mixture left 1 day at room temperature. The solution was mixed with 4 liters of water, stirred several hours, filtered and the ether separated, washed, dried and concentrated. The ether residue was taken up in a small amount of ether, filtered to remove solid, concentrated and distilled to give 37 gm. $b_{0.025}$ 64°–73°.

Preparation of 1-Adamantyl-2-propanone oxime VIII

Adamantane-1-isopropyl ketone (60 gm.) in 314 ml. absolute alcohol was mixed with a solution of 52.5 gm. hydroxylamine hydrochloride in 314 ml. water, 60 ml. of 20% NaOH added in 5–10 ml. portions to give the final solution a pH of 7. The solution was refluxed 7 minutes, poured into 3 liters of water, stirred ½ hour and filtered. The solid was dissolved in 300 ml. petroleum ether and 300 ml. $CHCl_3$, washed with 5% $NaHCO_3$, dried and concentrated. The residue was recrystallized from hexane and dried under vacuum at 57° to give 59 gm., m.p. 96°–8°.

|        | C     | H     | N    |
|--------|-------|-------|------|
| Calcd.: | 75.31 | 10.21 | 6.76 |
| Found : | 75.52 | 10.54 | 6.54 |

Preparation of β-(1-Adamantyl)-α-methylethylamine, IX

1-Adamantyl-2-propanone oxime (59 gm.) was dissolved in 775 ml. acetic acid, 10 gm. $PtO_2$ added and the mixture hydrogenated at about 40 lbs. pressure. The solution was filtered and concentrated. The residue was dissolved in 2 liters of ether, added, over 5–10 minutes, to 84 gm. $NaHCO_3$ in 10 liters of water and stirred for ½ hour. The ether was separated and concentrated and the residue treated with 50 ml. acetic acid, and concentrated. The acetic acid residue was dissolved in 200 ml. ether, added to 8.4 gm. $NaHCO_3$ in 1 liter of water and this solution added to the main solution. NaOH (53 ml. of 50% solution) was added to the combined aqueous solutions, stirred 5 minutes and extracted with 2 × 1.5 liters of ether. The ether extract was dried and concentrated and the residue distilled to give 42.2 gm. product, $b_{25}$ 161°.

Preparation of β-(1-Adamantyl)-α-methylethylamine hydrochloride, X

β-(1-Adamantyl)-α-methylethylamine (13.3 gm.) was dissolved in 550 ml. anhydrous ether and acidified with HCl gas. The solid was filtered, dried under vacuum at 88°, dissolved in 150 ml. $CHCl_3$, and 850 ml. petroleum ether added to give 15 gm. product, m.p. 295°–7°.

|        | C     | H     | Cl    | N    |
|--------|-------|-------|-------|------|
| Calcd.: | 67.95 | 10.53 | 15.43 | 6.10 |
| Found : | 68.18 | 10.74 | 16.02 | 5.94 |
|        |       |       | 15.55 |      |
|        |       |       | 15.42 |      |

EXAMPLE 3

Resolution of β-(1-Adamantyl)-β-methylethylamine into d-β-(1-Adamantyl)-α-methylethylamine and l-β-(1-Adamantyl)-α-methylethylamine β-(1-Adamantyl)-α-methylethylamine (25 g.) was added to a boiling solution of 19.5 gm. d-tartaric acid in 2.5 liters of absolute alcohol. The solution was cooled to room temperature and filtered to give 42 gm. of amine tartrate. This was boiled with 2.2 liters of alcohol and filtered to give a solution (A) and an undissolved solid (B). The solid was recrystallized twice from alcohol to give 4.9 gm. solid (C). Solution (A) was cooled to give a solid which, combined with solids from other experiments, was dissolved in water, treated with NaOH, extracted with ether, and the ether residue distilled to give 14.3 gm. (D), $b_{0.075}$ 130°–6°. The amine (D) was treated as above with 11.1 gm. l-tartaric acid and the hot solution cooled to 50° and filtered to give 12.6 gm. of amine tartrate (E). The filtrate was concentrated to dryness and the residue, with other fractions, was converted to the base and distilled to give 10.3 gm. amine. The amine (10.3 gm.) was treated as above with d-tartaric acid and filtered at 40° to give the amine tartrate (F). The filtrate was taken to dryness to give residue (G). The tartrate (F) was recrystallized from 400 ml. methanol to give 2.5 gm. (H), a 2nd crop of 0.7 gm. (I), a 3rd crop of 0.7 gm. (J), and the mother liquor residue (K). Combined (G) and (K) were converted to the base and distilled to give 6 gm. amine which was treated with 1-tartaric acid. The tartrate was recrystallized from methanol to give 1.8 gm. 1st crop (L) and 2.5 gm. 2nd crop which was recrystallized again to give 0.9 gm. (M). E, L, and M were combined and recrystallized from 850 ml. methanol to give 8 gm. 1st crop and 3.7 gm. 2nd crop which were combined, converted to base with NaOH and distilled. The d-amine (5.8 gm.) was dissolved in anhydrous ether and treated with HCl gas to give 5.7 gm. of the d-$\beta$-(1-Adamantyl-$\alpha$-methylamine hydrochloride, m.p. 301°–3°. C, H, I, and J were combined, converted to the base, the base extracted with ether, the ether dried and acidified with HCl gas to give the 1-$\beta$-(1-Adamantyl)-$\alpha$-methylamine hydrochloride. This was dissolved in 50 ml. CHCl$_3$ and precipitated with petroleum ether to give 4.5 gm., m.p. 298°–300°.

ADDITIONAL EXAMPLES $\beta$-(1Adamantyl-$\alpha,\alpha$-dimethylethylamine
$\beta$-[1-(3-Ethyladamantyl]-$\alpha,\alpha$-dimethylethylamine
$\beta$-[1-(3Hydroxyadamantyl)]-$\alpha,\alpha$-dimethylethylamine
$\beta$-[1-(3,5,7-Trimethyladamantyl)]-$\alpha,\alpha$-dimethylethylamine
$\beta$-[1-(3-Chloroadamantyl)]-$\alpha,\alpha$-dimethylethylamine
$\beta$-[1-(3-Aminoadamantyl)]-$\alpha,\alpha$-dimethylethylamine
$\beta$-[1-(3-Methyladamantyl)]-$\alpha,\alpha$-dimethylethylamine
$\beta$-(1-Adamantyl)-$\beta$-hydroxy-$\alpha,\alpha$-dimethylethylamine
$\alpha$-(1-Adamantylcarbonyl)-$\alpha$-methylethylamine
d-$\beta$-(1Adamantyl)-$\beta$-hydroxy-$\alpha,\alpha$-dimethylethylamine
1-$\beta$-(1Adamantyl)-$\beta$-hydroxy-$\alpha,\alpha$-dimethylethylamine
$\beta$-(1Adamantyl)-$\alpha,\alpha$-dimethyl-4-ethylmorpholine
$\beta$-(1-Adamantyl)-$\alpha,\alpha$-dimethyl-1-ethylpiperazine
$\beta$-(1-Adamantyl)-$\alpha,\alpha$-dimethyl-1-ethylpiperidine
$\beta$-(1-Adamantyl)-$\alpha,\alpha$-dimethyl-1-ethylpyrrolidine
$\beta$-(1-Adamantyl)-ethylamine
Methyl-$\beta$-(1-adamantyl)-ethylcarbamate
Ethyl-$\beta$-(1-adamantyl)-ethylcarbamate
Methyl-$\beta$-(1-adamantyl)-$\alpha,\alpha$-dimethylethyl carbamate
Ethyl-$\beta$-(1-adamantyl)-$\alpha,\alpha$-dimethylethyl carbamate
Methyl-$\beta$-(1adamantyl)-$\alpha$-methylethyl carbamate
Ethyl-$\beta$-(1-adamantyl)-$\alpha$-methylethyl carbamate
$\beta$-(1-Adamantyl)-$\alpha$-methylethylamine
d-$\beta$-(1-Adamantyl)-$\alpha$-methylethylamine
1-$\beta$-(1-Adamantyl)-$\alpha$-methylethylamine
$\beta$-[1-(3-Ethyladamantyl)]-$\alpha$-methylethylamine
d-$\beta$-[1-(3-Ethyladamantyl)]-$\alpha$-methylethylamine
1-$\beta$-[1-(3-Ethyladamantyl)]-$\alpha$-methylethylamine
$\beta$-[1-(3-Hydroxyadamantyl)]-$\alpha$-methylethylamine
d-$\beta$-[1-(3-Hydroxyadamantyl)]-$\alpha$-methylethylamine
1-$\beta$-[1-(3-Hydroxyadamantyl)]-$\alpha$-methylethylamine
$\beta$-[1-(3,5,7-Trimethyladamantyl)]-$\alpha$-methylethylamine
d-$\beta$-[1-(3,5,7-Trimethyladamantyl)]-$\alpha$-methylethylamine
1-$\beta$-[1-(3,5,7-Trimethyladamantyl)]-$\alpha$-methylethylamine
$\beta$-[1-(3-Chloroadamantyl)]-$\alpha$-methylethylamine
d-$\beta$-[1-(3-Chloroadamantyl)]-$\alpha$-methylethylamine
1-$\beta$-[1-(3-Chloroadamantyl)]-$\alpha$-methylethylamine
$\beta$-[1-(3-Aminoadamantyl)]-$\alpha$-methylethylamine
d-$\beta$-[1-(3-Aminoadamantyl)]-$\alpha$-methylethylamine
1-$\beta$-[1-(3-Aminoadamantyl)]-$\alpha$-methylethylamine
$\beta$-[1-(3-Methyladamantyl)]-$\alpha$-methylethylamine
d-$\beta$-[1-(3-Methyladamantyl)]-$\alpha$-methylethylamine
1-$\beta$-[1-(3-Methyladamantyl)]-$\alpha$-methylethylamine
$\beta$-(1-Adamantyl)-$\beta$-hydroxy-$\alpha$-methylethylamine
d-$\beta$-(1-Adamantyl)-$\beta$-hydroxy-$\alpha$-methylethylamine
1-$\beta$-(1-Adamantyl)-$\beta$-hydroxy-$\alpha$-methylethylamine
$\beta$-(1-adamantyl)-$\beta$-oxo-$\alpha$-methylethylamine
d-$\alpha$-(1-Adamantylcarboxy)-$\alpha$-ethylethylamine
1-$\alpha$-(1-Adamantylcarbonyl)-$\alpha$-ethylethylamine
$\beta$-(1-Adamantyl)-$\alpha$-methyl-4-ethylmorpholine
d-$\beta$-(1-Adamantyl)-$\alpha$-methyl-4-ethylmorpholine
1-$\beta$-(1-Adamantyl)-$\alpha$-methyl-4-ethylmorpholine
$\beta$-(1-Adamantyl)-$\alpha$-methyl-1-ethylpiperazine
d-$\beta$-(1-Adamantyl)-$\alpha$-methyl-1-ethylpiperazine
1-$\beta$-(1-Adamantyl)-$\alpha$-methyl-1-ethylpiperazine
$\beta$-(1-Adamantyl)-$\alpha$-ethynylethylamine
d-$\beta$-(1-Adamantyl)-$\alpha$-ethynylethylamine
1-$\beta$-(1-Adamantyl)-$\alpha$-ethynylethylamine
$\beta$-(1-Adamantyl)-$\alpha$-methyl-1-ethylpiperidine
d-$\beta$-(1-Adamantyl)-$\alpha$-methyl-1-ethylpiperidine
1-$\beta$-(1-Adamantyl)-$\alpha$-methyl-1-ethylpiperidine
$\beta$-(1-Adamantyl)-$\alpha$-methyl-1-ethylpyrrolidine
d-$\beta$-(1-Adamantyl)-$\alpha$-methyl-1-ethylpyrrolidine
1-$\beta$-(1-Adamantyl)-$\alpha$-methyl-1-ethylpyrrolidine
$\beta$-(1-Adamantyl)-N-formyl)-$\alpha$-methylethylamine
$\beta$-(1-Adamantyl)-$\alpha,\alpha$-dimethyl-N-formylethylamine
N-Acetyl-$\beta$-(1-adamantyl)-$\alpha$-methylethylamine
N-Acetyl-$\beta$-(1-adamantyl)-$\alpha,\alpha$-dimethylethylamine

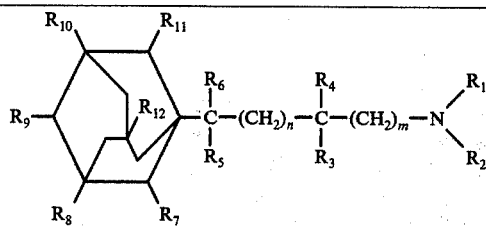

| $R_1$ | $R_2$ | $R_3$ | $R_4$ | $R_5$ | $R_6$ | $R_7$ | $R_8$ | $R_9$ | $R_{10}$ | $R_{11}$ | $R_{12}$ | m or n |
|---|---|---|---|---|---|---|---|---|---|---|---|---|
| Me | H | H | H | H | H | H | H | H | H | H | Me | 0 |
| Et | H | H | H | H | H | H | H | H | H | H | Cl | 0 |
| Pr | H | H | H | H | H | H | H | H | H | H | OH | 0 |
| H | Me | H | H | H | H | H | H | H | H | H | OMe | 0 |
| H | Et | H | H | H | H | H | H | H | H | H | NH$_2$ | 0 |
| H | Pr | H | H | H | H | H | H | H | H | H | NMe$_2$ | 0 |
| Me | Me | H | H | H | H | H | H | H | H | H | CF$_3$ | 0 |
| Me | Et | H | H | H | H | H | H | H | H | H | H | 0 |
| Et | Et | H | H | H | H | H | H | H | H | H | H | 0 |
| H | H | Et | H | H | H | H | H | H | H | H | H | 0 |

-continued

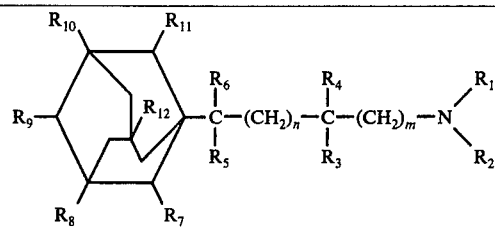

| $R_1$ | $R_2$ | $R_3$ | $R_4$ | $R_5$ | $R_6$ | $R_7$ | $R_8$ | $R_9$ | $R_{10}$ | $R_{11}$ | $R_{12}$ | m or n |
|---|---|---|---|---|---|---|---|---|---|---|---|---|
| Me | Me | Me | H | H | H | H | H | H | H | H | H | 0 |
| H | H | H | Et | H | H | H | H | H | H | H | H | 1 |
| Me | H | H | Me | H | H | H | H | H | H | H | H | 2 |
| Me | Me | H | Me | H | H | H | H | H | H | H | H | 3 |
| Me | Me | Me | Me | H | H | H | H | H | H | H | H | 4 |
| H | H | H | H | OH | H | H | H | H | H | H | H | 0 |
| H | H | H | H | Cl | H | H | H | H | H | H | H | 0 |
| H | H | H | H | Br | H | H | H | H | H | H | H | 0 |
| H | H | H | H | F | H | H | H | H | H | H | H | 0 |
| H | H | H | H | Me | H | H | H | H | H | H | H | 0 |
| H | H | H | H | Et | H | H | H | H | H | H | H | 0 |
| Me | Me | H | H | OH | H | H | H | H | H | H | H | 0 |
| Me | Me | H | H | Cl | H | H | H | H | H | H | H | 0 |
| Me | Me | H | H | Br | H | H | H | H | H | H | H | 0 |
| Me | Me | H | H | F | H | H | H | H | H | H | H | 0 |
| Me | Me | H | H | Me | H | H | H | H | H | H | H | 0 |
| Me | Me | H | H | Et | H | H | H | H | H | H | H | 0 |
| H | H | H | H | H | OH | H | H | H | H | H | H | 0 |
| H | H | H | H | H | Cl | H | H | H | H | H | H | 0 |
| H | H | H | H | H | Br | H | H | H | H | H | H | 0 |
| H | H | H | H | H | F | H | H | H | H | H | H | 0 |
| Me | Me | H | H | H | OH | H | H | H | H | H | H | 0 |
| Me | Me | H | H | H | Cl | H | H | H | H | H | H | 0 |
| Me | Me | H | H | H | Br | H | H | H | H | H | H | 0 |
| Me | Me | H | H | H | F | H | H | H | H | H | H | 0 |
| H | H | H | H | H | Me | H | H | H | H | H | H | 0 |
| H | H | H | H | H | Et | H | H | H | H | H | H | 0 |
| Me | Me | H | H | H | Me | H | H | H | H | H | H | 0 |
| Me | Me | H | H | H | Et | H | H | H | H | H | H | 0 |
| H | H | H | H | H | H | Me | H | H | H | H | H | 0 |
| H | H | H | H | H | H | Et | H | H | H | H | H | 0 |
| H | H | H | H | H | H | Pr | H | H | H | H | H | 0 |
| H | H | H | H | H | H | Cl | H | H | H | H | H | 0 |
| H | H | H | H | H | H | Br | H | H | H | H | H | 0 |
| H | H | H | H | H | H | F | H | H | H | H | H | 0 |
| H | H | H | H | H | H | OH | H | H | H | H | H | 0 |
| H | H | H | H | H | H | OMe | H | H | H | H | H | 0 |
| H | H | H | H | H | H | OEt | H | H | H | H | H | 0 |
| H | H | H | H | H | H | $NH_2$ | H | H | H | H | H | 0 |
| H | H | H | H | H | H | NHMe | H | H | H | H | H | 0 |
| H | H | H | H | H | H | $NMe_2$ | H | H | H | H | H | 0 |
| H | H | H | H | H | H | $CF_3$ | H | H | H | H | H | 0 |
| H | H | H | H | H | H | H | Me | H | H | H | H | 0 |
| H | H | H | H | H | H | H | Et | H | H | H | H | 0 |
| H | H | H | H | H | H | H | Pr | H | H | H | H | 0 |
| H | H | H | H | H | H | H | Cl | H | H | H | H | 0 |
| H | H | H | H | H | H | H | Br | H | H | H | H | 0 |
| H | H | H | H | H | H | H | F | H | H | H | H | 0 |
| H | H | H | H | H | H | H | OH | H | H | H | H | 0 |
| H | H | H | H | H | H | H | OMe | H | H | H | H | 0 |
| H | H | H | H | H | H | H | OEt | H | H | H | H | 0 |
| H | H | H | H | H | H | H | $NH_2$ | H | H | H | H | 0 |
| H | H | H | H | H | H | H | $NMe_2$ | H | H | H | H | 0 |
| H | H | H | H | H | H | H | NHMe | H | H | H | H | 0 |
| H | H | H | H | H | H | H | $CF_3$ | H | H | H | H | 0 |
| H | H | H | H | H | H | H | H | Me | H | H | H | 0 |
| H | H | H | H | H | H | H | H | Et | H | H | H | 0 |
| H | H | H | H | H | H | H | H | Pr | H | H | H | 0 |
| H | H | H | H | H | H | H | H | Cl | H | H | H | 0 |
| H | H | H | H | H | H | H | H | Br | H | H | H | 0 |
| H | H | H | H | H | H | H | H | F | H | H | H | 0 |
| H | H | H | H | H | H | H | H | OH | H | H | H | 0 |
| H | H | H | H | H | H | H | H | OMe | H | H | H | 0 |
| H | H | $CH_3$ | $CH_3$ | H | H | H | H | $CH_3$ | H | $CH_3$ | $CH_3$ | 0 |
| H | H | $CH_3$ | H | H | H | H | H | $CH_3$ | H | $CH_3$ | $CH_3$ | 0 |
| H | H | H | H | H | H | H | H | NHMe | H | H | H | 0 |
| H | H | H | H | H | H | H | H | $NMe_2$ | H | H | H | 0 |
| H | H | H | H | H | H | H | H | $CF_3$ | H | H | H | 0 |
| H | H | $CH_3$ | $CH_3$ | H | H | H | H | H | OH | H | H | 0 |
| H | H | $CH_3$ | H | H | H | H | H | H | OH | H | H | 0 |
| H | H | $CH_3$ | $CH_3$ | H | H | H | H | H | $OCH_3$ | H | H | 0 |
| H | H | $CH_3$ | H | H | H | H | H | H | $OCH_3$ | H | H | 0 |
| H | H | $CH_3$ | $CH_3$ | H | H | H | H | H | Br | H | H | 0 |
| H | H | $CH_3$ | H | H | H | H | H | H | F | H | H | 0 |
| H | H | $CH_3$ | $CH_3$ | H | H | H | H | H | Cl | H | H | 0 |
| H | H | $CH_3$ | H | H | H | H | H | H | Cl | H | H | 0 |
| H | H | $CH_3$ | $CH_3$ | H | H | H | H | H | $NH_2$ | H | H | 0 |
| H | H | $CH_3$ | H | H | H | H | H | H | $NH_2$ | H | H | 0 |
| H | H | $CH_3$ | $CH_3$ | H | H | H | H | H | NHMe | H | H | 0 |
| H | H | $CH_3$ | H | H | H | H | H | H | $NMe_2$ | H | H | 0 |

-continued

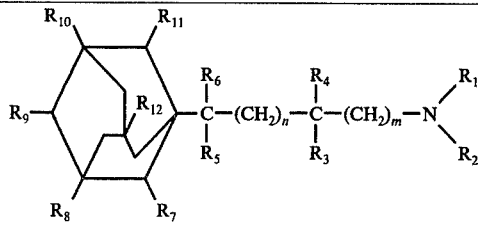

| R₁ | R₂ | R₃ | R₄ | R₅ | R₆ | R₇ | R₈ | R₉ | R₁₀ | R₁₁ | R₁₂ | m or n |
|---|---|---|---|---|---|---|---|---|---|---|---|---|
| H | H | CH₃ | CH₃ | H | H | H | H | H | CF₃ | H | H | 0 |
| H | H | CH₃ | H | H | H | H | H | H | CF₃ | H | H | 0 |
| H | H | H | H | H | H | H | H | H | H | Et | H | 0 |
| H | H | H | H | H | H | H | H | H | H | Pr | H | 0 |
| H | H | H | H | H | H | H | H | H | H | Cl | H | 0 |
| H | H | H | H | H | H | H | H | H | H | Br | H | 0 |
| H | H | H | H | H | H | H | H | H | H | F | H | 0 |
| H | H | H | H | H | H | H | H | H | H | OH | H | 0 |
| H | H | H | H | H | H | H | H | H | H | OEt | H | 0 |
| H | H | H | H | H | H | H | H | H | H | NH₂ | H | 0 |
| H | H | H | H | H | H | H | H | H | H | NHMe | H | 0 |
| H | H | H | H | H | H | H | H | H | H | NMe₂ | H | 0 |
| H | H | CH₃ | H | H | H | H | H | H | H | CF₃ | H | 0 |
| H | H | CH₃ | CH₃ | H | H | H | H | H | H | H | H | 1 |
| H | H | CH₃ | H | H | H | H | H | H | H | H | H | 1 |
| CH(CH₃)₂ | H | CH₃ | H | H | H | H | H | H | H | H | H | 0 |
| CH(CH₃)₂ | CH(CH₃)₂ | CH₃ | H | H | H | H | H | H | H | H | H | 0 |
| CH(CH₃)₂ | H | CH₃ | CH₃ | H | H | H | H | H | H | H | H | 0 |
| CH(CH₃)₂ | CH(CH₃)₂ | CH₃ | CH₃ | H | H | H | H | H | H | H | H | 0 |
| (CH₂)₅ | | CH₃ | CH₃ | H | H | H | H | H | H | H | H | 0 |
| (CH₂)₄ | | CH₃ | H | H | H | H | Cl | H | H | H | H | 0 |
| (CH₂)₃ | | CH₃ | CH₃ | H | H | H | Cl | H | H | H | H | 0 |
| (CH₂)₃ | | CH₃ | H | H | H | H | H | H | H | H | H | 0 |
| (CH₂)₂O(CH₂)₂ | | H | H | H | H | H | H | H | H | H | H | 0 |
| (CH₂)₂NH(CH₂)₂ | | H | H | H | H | H | H | H | H | H | H | 0 |
| (CH₂)₂N(Me)(CH₂)₂ | | H | H | H | H | H | H | H | H | H | H | 0 |
| (CH₂)₂N(Ph)(CH₂)₂ | | H | H | H | H | H | H | H | H | H | H | 0 |
| —CH₂CH₂OCH₂CH₂— | | Me | H | H | H | H | H | H | H | H | H | 0 |
| —CH₂CH₂OCH₂CH₂— | | Me | Me | H | H | H | H | H | H | H | H | 0 |
| —(CH₂)₅— | | Me | H | H | H | H | H | H | H | H | H | 0 |
| —(CH₂)₅— | | Me | Me | H | H | H | H | H | H | H | H | 0 |
| —CH₂CH₂NHCH₂CH₂— | | Me | H | H | H | H | H | H | H | H | H | 0 |
| —CH₂CH₂NHCH₂CH₂— | | Me | Me | H | H | H | H | H | H | H | H | 0 |
| —CH₂CH₂N(Ph)CH₂ CH₂— | | Me | H | H | H | H | H | H | H | H | H | 0 |
| —CH₂CH₂N(Ph)CH₂ CH₂— | | Me | Me | H | H | H | H | H | H | H | H | 0 |
| —CH₂CH₂SCH₂CH₂— | | Me | H | H | H | H | H | H | H | H | H | 0 |
| —CH₂CH₂SCH₂CH₂— | | Me | Me | H | H | H | H | H | H | H | H | 0 |

Me = methyl
Et = ethyl
Pr = propyl

The following gives the structural formulae followed by exemplary specific compounds, illustrating a subclass of compounds under the generic formula which are effective anorectic agents.

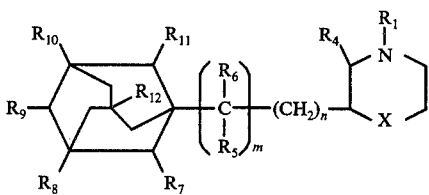

where n, R₁, R₄, R₅, R₆, R₇, R₈, R₉, R₁₀, R₁₁, R₁₂ are the same as given in the general structural formula first above written, X = O or S, and m = zero or 1

2-(1-Adamantylmethyl)-3-ethylmorpholine
2-(1-Adamantylmethyl)-3,4-dimethylmorpholine
2-(1-Adamantylmethyl)-morpholine
2-(1-Adamantylmethyl)-3-methylmorpholine
2-(1-Adamantylmethyl)-4-methylmorpholine
2-(1-Adamantylmethyl)-4-benzyl-3-methylmorpholine
2-(1-Adamantylmethyl)-4-benzylmorpholine
2-(1-[3,5,7-Trimethyladamantyl]-methyl)-3,4-dimethylmorpholine
2-(1-[3,5,7-Trimethyladamantyl]-methyl)-3-methylmorpholine
2-(1-[3-Hydroxyadamantyl]-methyl)-3-methylmorpholine
2-(1-[3-Chloroadamantyl]-methyl)-3-methylmorpholine
2-(1-Adamantylmethyl)-3-methylthiomorpholine
2-(1-Adamantyl)-3-methylmorpholine
2-(1-Adamantyl)-3-ethylmorpholine
2-(1-Adamantyl)-3-methylthiomorpholine
2-(1-Adamantyl)-4-benzyl-3-methylmorpholine
2-(1-[3-Chloroadamantyl])-3-methylmorpholine
2-(1-[3-Hydroxyadamantyl])-3-methylmorpholine
3-Methyl-2-(1-[3,5,7-trimethyladamantyl]) morpholine
2-(1-Adamantyl)-4-benzylmorpholine

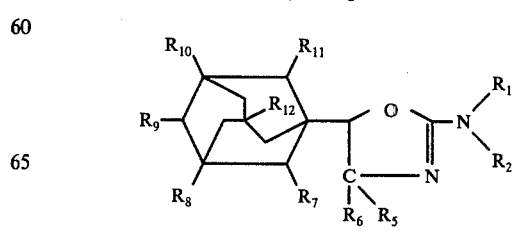

where $R_1$, $R_2$, $R_5$, $R_6$, $R_7$, $R_8$, $R_9$, $R_{10}$, $R_{11}$, $R_{12}$ are the same as given in the general formula first above written 5-(1-Adamantyl)-2-amino-2-oxazoline
5-(1-Adamantyl)-2-methylamino-2-oxazoline
5-(1-Adamantyl)-2-benzylamino-2-oxazoline
5-(1-Adamantyl)-2-isopropylamino-2-oxazolin-4-one
2-Isopropylamino-5-(1-[3,5,7-trimethyladamantyl])-2-oxazolin-4-one
5-(1-Adamantyl)-2-propylamino-2-oxazoline
5-(1-Adamantyl)-2-isopropylamino-2-oxazoline
2-Amino-5-(1-[3,5,7-trimethyladamantyl])-2-oxazoline
5-(1-Adamantyl)-2-propylamino-2-oxazolin-4-one
5-(1-Adamantyl)-2-amino-2-oxazolin-4-one
2-Amino-5-(1-[3,5,7-trimethyladamantyl])-2-oxazolin-4-one
2-Amino-5-(1-[3-chloroadamantyl]) -2-oxazoline
2-Amino-5-(1-[3-hydroxyadamantyl])-2-oxazoline
5-(1-[3-Chloroadamantyl])-2-isopropylamino-2-oxazolin-4-one
5-(1-[3-Hydroxyadamantyl])-2-isopropylamino-2-oxazoline-4-one

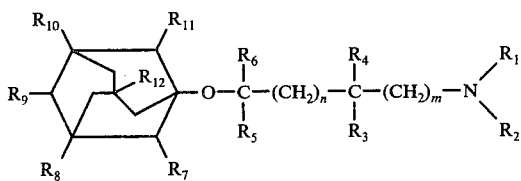

where $m$, $n$, $R_1$, $R_2$, $R_3$, $R_4$, $R_5$, $R_6$, $R_7$, $R_8$, $R_9$, $R_{10}$, $R_{11}$, $R_{12}$ are the same as given in the general structural formula first above written.

β-(1-Adamantyloxy)-α-methylethylamine
d-β-(1-Adamantyloxy)-α-methylethylamine
l-β-(1-Adamantyloxy)-α-methylethylamine
β-(1-Admantyloxy)-α-Adamantyloxy)-α-dimethylethylamine
β-(1-[3-Chloroadamantyloxy])-α,α-dimethylethylamine
β-(1-[3-Hydroxyadamantyloxy])-α,α-dimethylethylamine
α,α-Dimethyl-β-(1-[3,5,7-trimethyladamantyloxy])-ethylamine
β-(1-Adamantyl)-N,α,α-trimethylethylamine The above compounds of this case can be used as intermediates for the synthesis of the hydrazine derivatives by methods well known to the art for preparing hydrazine derivatives from similar amine compounds. These hydrazine derivatives are hypotensive agents, and monoamine oxidase inhibitors.

The principal use, however, for the compounds is in the curbing of appetite in animals.

The following are illustrative examples of anorectic preparations.

EXAMPLE 4

Hard gelatine capsules containing the following ingredients are prepared as follows:

|  | Mg. |
|---|---|
| β-(1-adamantyl)-α,α-dimethylethylamine hydrochloride | 5 |
| lactose | 200 |
| Magnesium stearate | 2 |

The ingredients are mixed, screened, and dry filled into capsules.

EXAMPLE 5

A tablet having the following composition is prepared as follows:

|  | Mg. |
|---|---|
| β-(1-adamantyl)-α-methylethylamine hydrochloride | 15 |
| Microcrystalline cellulose | 50 |
| Lactose | 40 |
| Starch | 15 |
| Magnesium stearate | 2 |

The adamantyl compound, lactose, and microcrystalline cellulose are mixed and granulated with a portion of the starch as a 10% solution. The granules are screened to +16 mesh and dried. After rescreening to +20 mesh, the balance of the starch and magnesium stearate are added and the mixture compressed.

EXAMPLE 6

A syrup having the following composition is prepared as follows:

|  | Mg. |
|---|---|
| β-(1-adamantyl)-α-methylethylamine hydrochloride | 50 |
| Sorbitol solution, 70% | 50 ml. |
| Buffer (dibasic sodium phosphate and citric acid) q.s. to pH 5.5. | |
| Orange flavor | 10 |
| Distilled water q.s. to 100 ml. | |

All the ingredients are mixed and dissolved in water to form a syrup. Three teaspoons of the syrup are administered orally to obese persons three times daily to induce anorexia.

EXAMPLE 7

A sustained release preparation having the following composition is prepared as follows:

|  | Mg. |
|---|---|
| The resin addition salt of a crosslinked sulfonic acid cation exchange resin (Amberlite IR-120) and β-(1-adamantyl)-α,α-dimethylethylamine containing 30% of the amine | 40 |
| Lactose | 425 |
| Magnesium stearate | 2 |

The ingredients are mixed, screened, and dry filled into capsules.

Anorectic Screening Study With Compounds 748-534 [β-(1-adamantyl)-α-methylethylamine hydrochloride] and 741-976-A [β-(1-adamantyl)-α,α-dimethylethylamine hydrochloride]

Compounds No. 748-534 (50 mg./Kg. P.O.) and 741-976-A (5 mg./Kg. I. P.) were administered to 450 gram Sprague-Dawley male rats according to the following schedule:

The animals were placed in group cages, five rats/group, and fed ad libitum with powdered pellet diet. Normal average daily food consumption measurements were recorded prior to starting the drug treatment. The rats were dosed each morning for five days and the daily food consumption was measured. They were then fasted overnight and on the following morning a sixth dose was given to each group. One hour after the drug was given, food was presented to the animals and its consumption was measured 1, 2, 3, and 5 hours later.

In this study, compound No. 748-534 inhibited food intake 44% and compound No. 741-976-A inhibited food intake 38%, respectively as compared to the untreated animal group over the five-hour period as shown in the graph of the accompanying drawing. During the course of the five-day treatment where food was fed ad libitum there were no significant changes of food consumption between the groups over the 24-hour periods.

The anorectic activity of the above compounds is exemplary of the activity of the other compounds disclosed in this case and coming under the generic formulae above written; there being variations in the activity of the different compounds, but all being suitable for curbing appetite in animals at nontoxic dosages.

I claim:

1. The method of curbing appetite in an animal which comprises administering to the animal an amount effective to curb appetite of a compound of the formula:

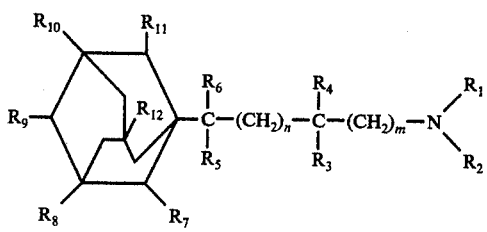

or their pharmaceutically acceptable acid addition salts, in which $R_1$ = H, lower alkyl, aralkyl, aralkyl substituted with $NH_2$, OH, $OCH_3$, halogen, alkyl, $NO_2$; phenoxyalkyl or phenoxyalkyl substituted with $NH_2$, OH, $OCH_3$, halogen, alkyl, or $NO_2$; acyl including formyl or acetyl;

$R_2$ = H, lower alkyl, COO-lower alkyl, aralkyl, aralkyl substituted with $NH_2$, OH, $OCH_3$, halogen, alkyl, $NO_2$; phenoxyalkyl or phenoxyalkyl substituted with $NH_2$, OH, $OCH_3$, halogen, alkyl, or $NO_2$; acyl including formyl or acetyl, $R_3$ = H, lower alkyl or alkynyl;

$R_4$ = H, lower alkyl, or alkynyl;

$R_5$ = H, OH, halogen, or lower alkyl;

$R_6$ = H, OH, halogen, or lower alkyl; or $R_5$ and $R_6$ together represent a carbonyl oxygen;

$R_7$ = H, lower alkyl, halogen, hydroxy, alkoxy, amino or substituted amino, trifluoromethyl, sulfamyl, nitro, phenyl;

$R_8$, $R_9$, $R_{10}$, $R_{11}$, $R_{12}$ are any of $R_7$;

$n$ = 0 to 4;

$m$ = 0 to 4;

2. The method of claim 1 in which the compound is $\beta$-(1-adamantyl)-$\alpha,\alpha$-dimethylethylamine or its acid addition salt.

3. The method of claim 1 in which the compound is $\beta$-(1-adamantyl)-$\alpha$-methylethylamine or its acid addition salt.

4. The method of claim 1 in which the compound is d-$\beta$-(1-adamantyl)-$\alpha$-methylethylamine or its acid addition salt.

5. The method of claim 1 in which the compound is 1-$\beta$-(1-adamantyl)-$\alpha$-methylethylamine or its acid addition salt.

* * * * *